United States Patent [19]
DiFilippo et al.

[11] Patent Number: 5,923,038
[45] Date of Patent: Jul. 13, 1999

[54] PARTIAL ANGLE TOMOGRAPHY SCANNING AND RECONSTRUCTION

[75] Inventors: Frank P. DiFilippo; Daniel Gagnon, both of Mayfield Heights, Ohio

[73] Assignee: Picker International, Inc., Cleveland, Ohio

[21] Appl. No.: 08/866,179

[22] Filed: May 30, 1997

[51] Int. Cl.$^6$ .................................................. G01T 1/166
[52] U.S. Cl. ..................................... 250/363.04; 600/425
[58] Field of Search .......................... 250/363.04, 363.02, 250/369; 600/425

[56] References Cited

U.S. PATENT DOCUMENTS 5,744,802  4/1998  Muehllehner et al. ............. 250/363.04
5,762,608  6/1998  Warne et al. ............................ 600/425

OTHER PUBLICATIONS

K.C. Tam, G. Chu, V. Perez–Mendex and C.B. Lim; "Three–Dimensional Reconstruction In Planar Positron Cameras Using Fourier Deconvolution Of Generalized Tomograms;" *IEEE Transactions on Nuclear Science*, vol. NS–25, No. 1, Feb. 1989, pp. 152–158.
K.C. Tam, V. Perez–Mendex; "Tomographical imaging with limited–angle input;" *J. Opt. Soc. Am*; vol. 71, No. 5; May 1981; pp. 582–592.

*Primary Examiner*—Edward P. Westin
*Assistant Examiner*—Richard D. Hanig
*Attorney, Agent, or Firm*—Timothy B. Gurin; John J. Fry

[57] ABSTRACT

A nuclear camera system includes oppositely disposed radiation detectors (10a, 10b) which view an examination region 14 wherein a subject 16 is received therein. During a diagnostic scan, a motor and drive assembly (18) concurrently moves the detectors (10a, 10b) in a straight path along a longitudinal axis (20) for a selected time interval. The radiation detectors (10a, 10b) are positioned at a first angle at which the subject is viewed and the angle is maintained through the scan. A data processor (23) collects the data from the detected radiation and a coincidence circuitry (26) determines coincidence radiation events occurring on the detectors 10a, 10b. A first set of image data is generated for the first angular view and stored in a view memory (28). A second scan is performed where the detectors (10a, 10b) are shifted to a second angular view and the detectors are moved along the longitudinal axis for a second selected time interval. Radiation data is collected and a second set of image data is generated for the second scan. The first and second sets of image data are combined and a reconstruction processor (50) reconstructs the combined data into an image representation or a whole-body tomographic image (60).

14 Claims, 3 Drawing Sheets

PARTIAL ANGLE TOMOGRAPHY SCANNING AND RECONSTRUCTION

BACKGROUND OF THE INVENTION

The present invention relates to the art of diagnostic imaging. It finds particular application in conjunction with nuclear or gamma cameras and will be described with particular reference thereto. It is to be appreciated, however, that the present invention will also find application in other non-invasive investigation techniques and imaging systems such as single photon planar imaging, whole body nuclear scans, positron emission tomography (PET), digital x-ray computed tomography and other diagnostic modes.

Single photon emission computed tomography (SPECT) has been used to study a radionuclide distribution in a subject. Typically, one or more radiopharmaceuticals or radioisotopes are injected into a patient subject. The radioisotope preferably travels to an organ of interest whose image is to be produced. The patient is placed in an examination region of the SPECT system surrounded by large area planar radiation detectors. Radiation emitted from the patient is detected by the radiation detectors. The detectors have a mechanical collimator to limit the detector to seeing radiation from a single selected trajectory or ray, often the ray normal to the detector plane.

Typically, the detector includes a scintillation crystal that is viewed by an array of photomultiplier tubes. The relative outputs of the photomultiplier tubes are processed and corrected, as is conventional in the art, to generate an output signal indicative of (1) a position coordinate on the detector head at which each radiation event is received, and (2) an energy of each event. The energy is used to differentiate between emission and transmission radiation and between multiple emission radiation sources and to eliminate stray and secondary emission radiation. A two-dimensional projection image representation is defined by the number of radiation events received at each coordinate.

In tomographic imaging, data collection is performed by either continuous rotation of the detectors or by "step-and-shoot" data acquisition where the detector is rotated at uniform intervals, typically 2 degree steps, over a 360 degree or 180 degree range. At each step position, radiation events or counts are acquired from a selected time interval. The data acquired from each step position (e.g. each projection view) are combined to reconstruct an image representation.

Positron emission tomography (PET) scanners are known as coincidence imaging devices. In planar coincidence imaging, two detectors oppose each other with a subject disposed between the detectors. The detectors view the subject along a longitudinal axis without rotation, otherwise known as limited angle tomography. Radiation events are detected on each detector and a coincidence circuitry compares and matches the events on each detector. Events on one detector which have a coincident event on the other detector are valid data and used in image reconstruction.

The above-mentioned acquisition protocols may not be optimal for a given imaging situation. Some angular detector positions offer more useful imaging information than other angles due to geometric effects, attenuation, scatter of radiation, and random coincidences. In a situation where the count rate is low, an optimal acquisition protocol will greatly improve image quality.

The present invention provides a new and improved data acquisition system and method for diagnostic imaging systems which overcomes the above-referenced problems and others.

SUMMARY OF THE INVENTION

In accordance with the present invention, a new and improved method and apparatus for diagnostic imaging is provided. A diagnostic imaging system includes a plurality of planar radiation detectors which oppose each other and have an image volume disposed therebetween. The image volume includes a radio isotope which emits radiation that is detected by the radiation detectors. At a first angular view, the radiation detectors are moved along a longitudinal axis and a first set of radiation data is collected over a first time interval. At a second angular view, the radiation detectors are moved along the longitudinal axis and a second set of radiation data is collected during a second time interval. An image representation is reconstructed from a combination of the first and second sets of radiation data.

In accordance with a more limited aspect of the present invention, the steps of positioning, moving, collecting and reconstructing are repeated for different angular views of the radiation detectors until a desired image representation is obtained.

In accordance with another aspect of the present invention, a method of collecting radiation data with a nuclear camera system which includes a plurality of radiation detectors disposed at an angle to each other and has a subject positioned therebetween. The nuclear camera system performs a diagnostic scan which includes moving the radiation detectors along a non-rotating path and detecting radiation for a selected time interval. A plurality of diagnostic scans are performed where the radiation detectors are shifted in a different angular position for each of the plurality of diagnostic scans. Radiation data is generated for each of the plurality of diagnostic scans based on the radiation detected and the radiation data from the plurality of diagnostic scans are combined to generate a set of combined radiation data which has an enlarged angular view.

In accordance with another aspect of the present invention, a diagnostic imaging system is provided for generating an image representation of a subject disposed in an examination region. The diagnostic imaging system includes radiation detecting means for detecting radiation from the examination region, a means for moving the radiation detecting means or the subject along a straight path at a first fixed angle of view, a means for generating radiation data based on the radiation detected at the first fixed angle of view, a means for selectively positioning the radiation detecting means at a second fixed angle of view such that the means for generating generates radiation data based on radiation detected at the second fixed angle of view along the straight path, and an image generating means for generating an image representation of a region of interest of the subject based on the radiation data from the first and second fixed angles of view.

One advantage of the present invention is that data acquisition is improved by selecting certain imaging views and collecting data at the selected view for a longer time interval than other views which optimizes imaging time, reduces scan times, and improves image quality and lesion detection for count-limited systems.

Another advantage of the present invention is that selectable temporal and spatial data acquisition protocols are provided.

Another advantage of the present invention is that it may be applied to collimated single photon imaging systems as well as coincidence imaging of positron-emitters.

Another advantage of the present invention is that mechanical motion of detectors is decreased as compared to step-and-shoot data acquisition.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
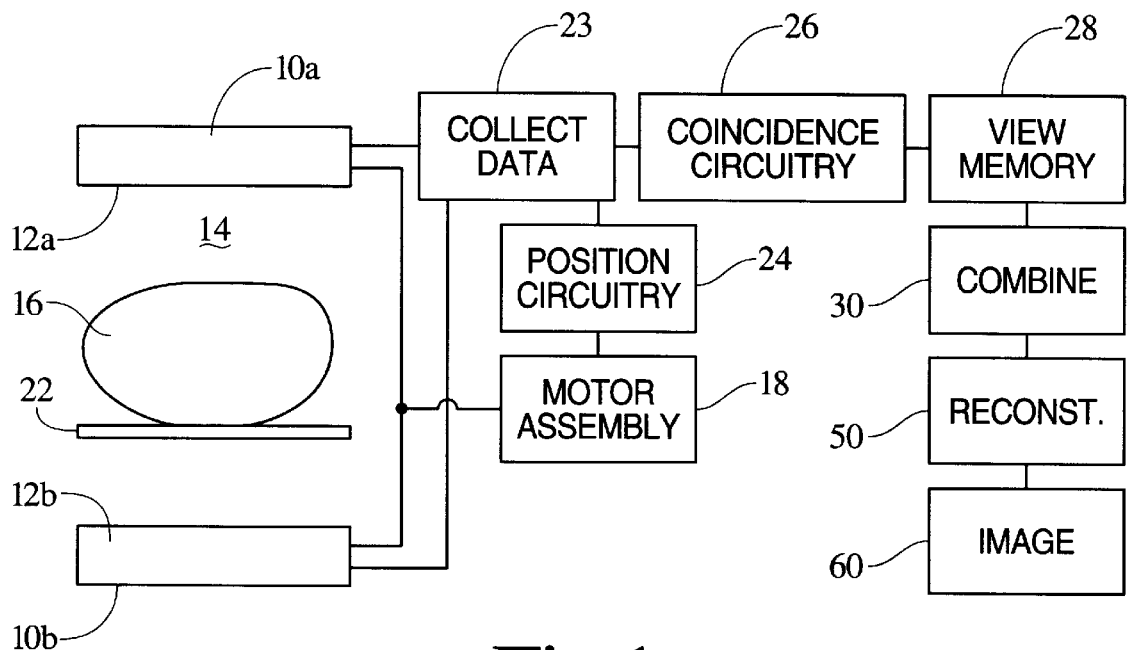
FIG. 1 is a diagrammatic illustration of a diagnostic imaging system in accordance with the present invention viewed along a longitudinal axis.
Figure 2:
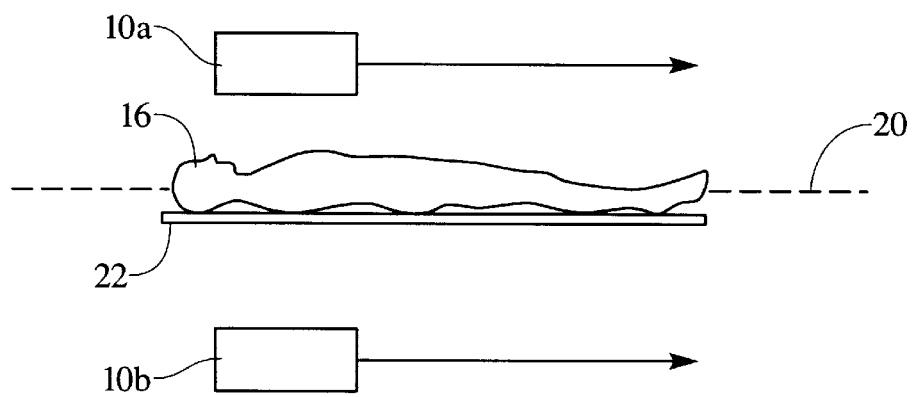
FIG. 2 is a side view of the diagnostic imaging system shown in FIG. 1.

With reference to FIGS. 1 and 2, a nuclear diagnostic imaging system has two planar radiation detectors 10a and 10b disposed at 180 degrees to each other and are supported on a movable gantry (not shown). Of course, the detectors may be positioned to oppose each other at any angle suitable for detecting radiation. A radiation receiving surface 12a and 12b of the detectors are positioned to view an examination region 14 for receiving a subject 16. It is to be appreciated that a greater or lessor number of detectors can be provided and detectors having non-planar radiation receiving surfaces can be used. The gantry includes a motor and drive assembly 18 which moves the radiation detectors concurrently along tracks in straight path along a longitudinal axis 20 which is along the length of the subject. The motor and drive assembly 18 also selectively rotates a rotatable portion of the gantry which concurrently adjusts an angular view of the detectors with respect to the subject. A subject support or patient couch 22 adjustably positions the subject in the examination region 14. Alternately, the gantry can be stationary and the subject support is configured to move the subject along the longitudinal axis.

In the preferred embodiment, each detector 10a, 10b includes a scintillation crystal that is viewed by an array of photomultiplier tubes. Radiation emanating from radiopharmaceuticals or other gamma radiation producing substances injected into the subject follows linear paths or rays outlined in radial directions from an isotope of the injected substance through the examination region 14 with radiation along a fraction of the rays being detected by the detectors 10a, 10b. Each time a radiation event occurs, radiation striking the scintillation crystal causes a light flash or scintillation. The photomultiplier tubes nearest the scintillation respond with proportional output signals. The gantry or an associated control console includes a data collection processor 23 for processing the data collected by the detectors 10a, 10b. Position and energy resolving circuitry 24 connected to the photomultiplier tubes determine the energy and position of each scintillation event. Position and energy resolving circuitry 24 also utilizes the longitudinal position of the detectors with respect to the subject.

In one embodiment, the injected substance includes a positron emitter which emits radiation in all directions, a fraction of which are detected by the detectors. A data processor collects data of each detection and a coincidence circuitry 26 compares and matches detected events on each of the detectors. For example, if an event on detector 10a has a coincidence event on detector 10b, the events are useful data and are stored in a view memory 28. Events which do not have a coincidence event are typically disregarded as noise. Alternately, a non-coincident event is used for image reconstruction if the event represents a single photon emission. For single photon emissions to occur, an isotope is present in the subject which has a different energy value than the positron emitter. Data collected from detected single photons are processes and reconstructed in any manner as is well-known in the art. Once the radiation data is collected, whether from coincidence, single photon emissions, or a combination of both, a reconstruction processor 50 reconstructs the data from the view memory into a selected image representation or a whole-body tomographic image 60. The image may be selectively displayed into a human readable form such as on a video display or on a printed medium.

Figure 3:
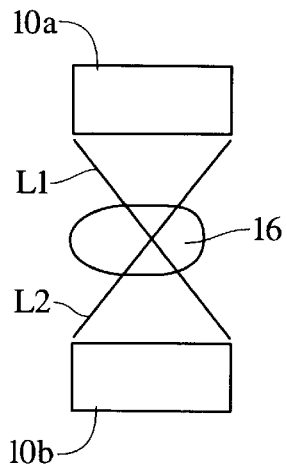
FIG. 3 is an example of radiation detectors set at a first angular view for a first scan.

With reference to FIGS. 3–6, an exemplary scan is shown where a scan includes moving the radiation detectors 10a, 10b along the longitudinal axis 20 and radiation data is collected for a selected time interval. In FIG. 3, the detectors 10a, 10b are positioned to view the examination region 14 at an initial angle or angular view. Lines L1 and L2 represent a limited angle area which is defined by the size and position of the detectors 10a, 10b. The motor assembly continuously moves the gantry, which thus moves both detectors, along a straight path following the longitudinal axis 20 for the selected time interval. The detectors are not rotated along the straight path. A reasonable scan interval for whole-body imaging is, for example, approximately 50 minutes which is partly limited by the inconvenience caused to the subject and time required to collect a sufficient amount of data. In the present scanning system however, the scan at the initial angular view is performed at a time interval, for example 30 minutes, which is less than a desired maximum scan time. The radiation data collected from the initial angular view is processed and stored in the view memory as a first set of angular view data.

After the initial angular views are obtained along the longitudinal axis 20, an operator may request the system to reconstruct an image based on the first set of angular view data obtained. If the resulting image is sufficient for a diagnosis, the scanning procedure can be stopped. Typically, however, additional data will be required.

Figure 4:
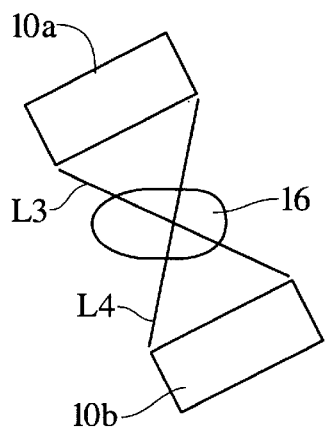
FIG. 4 is an example of radiation detectors set at a second angular view for a second scan.

With reference to FIG. 4, the scanning procedure is then continued with another diagnostic scan along the longitudinal axis 20 but here the radiation detectors 10a, 10b are positioned at a second angular view which is different from the initial angular view. The second angular view, which has an angular view area represented between lines L3 and L4, is obtained by rotating or translating the detectors 10a, 10b by a selected angle before the scan begins with the angle being maintained throughout the scan. The second scan is performed for a time interval which is selected based on the desired maximum time and the duration of the initial scan. For example, if the initial scan interval was 30 minutes, the second interval may be 10 minutes. Of course, the scan intervals may be any selected value and may equal one another. A second set of angular view data is obtained in a manner as described above. The first and second sets of angular view data are independently reconstructed and combined 30 (or vice-versa) in selective portions to generate a resultant image. Alternately, selected portions of the two sets of angular view data are combined 30 into a resultant data set which is then reconstructed into an image 60. By obtaining the second set of data, the system can progressively add to or enhance the previously obtained initial data in order to reconstruct more accurate images.

Figure 5:
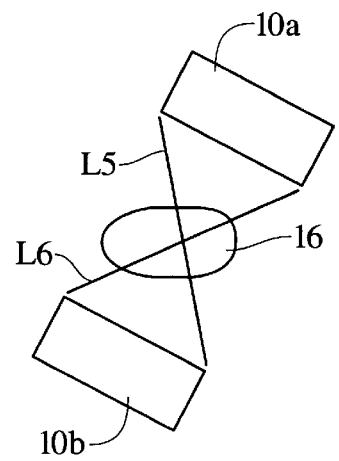
FIG. 5 is an example of radiation detectors set at a third angular view for a third scan.
Figure 6:
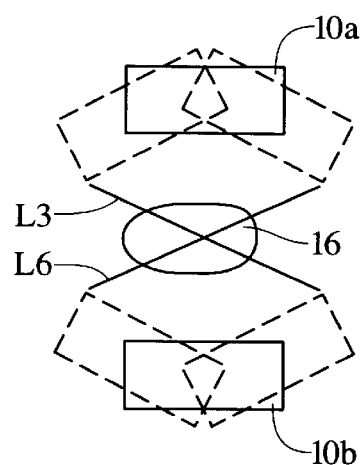
FIG. 6 is an example of a resultant angular view obtained from combining the views shown in FIGS. 3–5.

The process can be further iterated as shown in FIG. 5 where a third scan is performed with the detectors 10a, 10b positioned at a third angular view which has an angular view area defined by lines L5 and L6. As seen in FIGS. 3–5, for each individual scan, the detectors 10a, 10b have an equivalent angular view area which is defined and limited by the size of the detectors. However, combining the different sets of angular view data produces an enlarged angular view area represented by lines L3 and L6 as shown in FIG. 6 thus producing an improved sampling of data.

Figure 7:
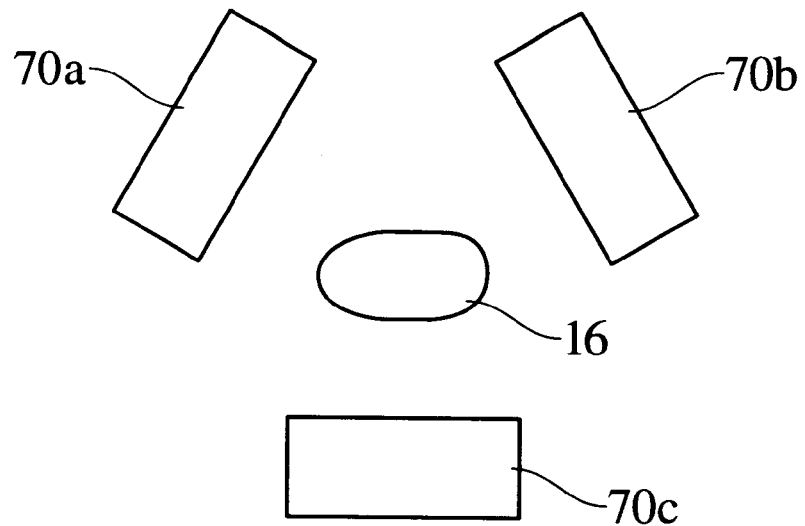
FIG. 7 is an example of three radiation detectors positioned for scan.
Figure 8:
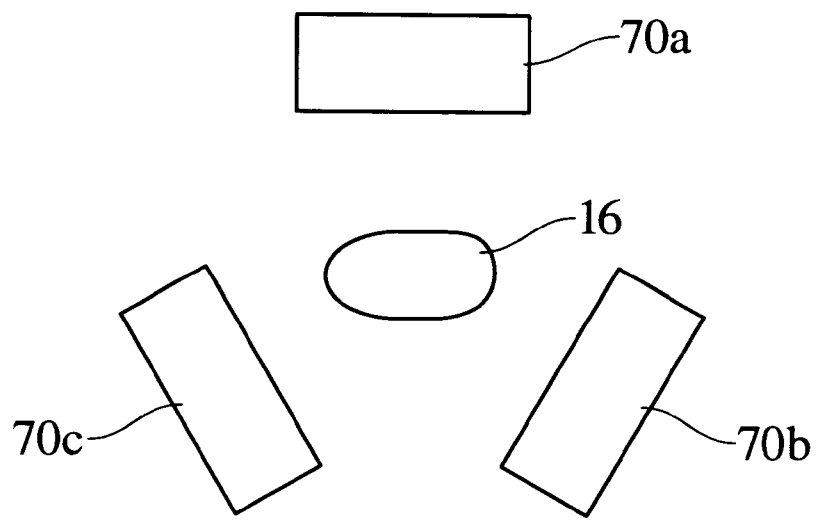
FIG. 8 shows the three radiation detectors of FIG. 7 positioned at another angular view for a second scan.

With reference to FIGS. 7 and 8, a three detector system is shown which has radiation detectors 70a, 70b, 70c mounted on the gantry 120 degrees from each other. A first diagnostic scan is performed as described above with the detectors 70a, 70b, 70c positioned at a first orientation angle having a first angular view as shown in FIG. 7. A second diagnostic scan is performed with the detectors 70a, 70b, 70c positioned at a second orientation angle having a second angular view as shown in FIG. 8 which is 60 degrees offset from the first orientation. Radiation data is collected during each scan and an image representation is reconstructed based on the two sets of data as previously described. Of course, additional scans may be performed at different angles until a desired image representation is obtained.

To optimize a given imaging situation, diagnostic scans at certain angular views are selected to have longer scanning intervals than other views or even by eliminating selected views completely from the acquisition procedure. Temporal and angular views can be varied from subject to subject. For example, in torso imaging, less body attenuation (and also less scatter) typically occurs in front-to-back views as opposed to side-to-side views. This results from the front-to-back depth of a subject being typically less than the side-to-side width. The result is that the counting efficiency is higher in a front view as compared to a side view. For another example, the additional angular views of partial angle tomography is more optimal than a single view scan, in many cases. The increased angular sampling yields more diagnostic image quality than the additional counts at the same view. Furthermore, since images can be reconstructed during data acquisition, an operator can adjust the selected angular views and scan intervals to focus on a region of interest.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of diagnostic imaging an object disposed in an image volume with a camera system including a plurality of radiation detectors opposing each other having the image volume disposed therebetween, the object including a radio-isotope for emitting radiation, the radiation being detected by the plurality of radiation detectors, the method comprising:

positioning the plurality of radiation detectors at a first angular view;

moving the plurality of radiation detectors along a longitudinal axis and collecting a first set of radiation data for a first time interval;

positioning the plurality of radiation detectors at a second angular view;

moving the plurality of detectors along the longitudinal axis and collecting a second set of radiation data for a second time interval; and reconstructing an image representation indicative of the object from a combination of the first and second sets of data.

2. The method of diagnostic imaging as set forth in claim 1 further including:

positioning the plurality of radiation detectors at a third angular view;

moving the radiation detectors along the longitudinal axis at the third angular view and collecting a third set of radiation data; and reconstructing an image representation based on a combination of the first, second and third sets of radiation data.

3. The method of diagnostic imaging as set forth in claim 1 further including repeating the steps of positioning, moving, collecting and reconstructing for different angular views of the radiation detectors until a desired image representation is obtained.

4. The method of diagnostic imaging as set forth in claim 1 wherein the collecting includes detecting coincidence radiation events on the plurality of radiation detectors.

5. The method of diagnostic imaging as set forth in claim 1 further including collimating radiation such that a selected path of radiation is detected by the radiation detectors.

6. The method of diagnostic imaging as set forth in claim 1 wherein the second time interval is different than the first time interval.

7. A method of imaging using a nuclear camera system including a plurality of radiation detectors disposed at an angle to each other and having a subject positioned therebetween, the subject including a radioisotope for emitting radiation, wherein a diagnostic scan includes moving the plurality of radiation detectors along a non-rotating path and detecting radiation for a selected time interval, the method comprising:

performing a plurality of diagnostic scans, the radiation detectors being shifted in a different angular position for each of the plurality of diagnostic scans;

generating radiation data for each of the plurality of diagnostic scans based on the radiation detected;

combining the radiation data from the plurality of diagnostic scans to generate a set of combined radiation data having an enlarged angular range;

reconstructing an image volume based on the combined radiation data.

8. The method of collecting radiation data during a diagnostic scan as set forth in claim 7 including performing first and second diagnostic scans where the plurality of radiation detectors are positioned at a first angular position during the first diagnostic scan and at a second angular position during the second diagnostic scan, the first and second angular positions being different from each other.

9. The method of collecting radiation data during a diagnostic scan as set forth in claim 7 wherein the generating is based on coincidence radiation events detected on the radiation detectors.

10. The method of collecting radiation data during a diagnostic scan as set forth in claim 7 wherein the generating is based on collimated radiation detected on the radiation detectors.

11. A diagnostic imaging system for generating an image representation of a subject disposed in an examination region, the diagnostic imaging system comprising:

radiation detecting means for detecting radiation emitted from the subject;

means for moving one of the subject and the radiation detecting means along a straight path where the radiation detecting means detects radiation at a first fixed angle of view;

means for generating radiation data based on the radiation detected at the first fixed angle of view;

means for selectively positioning the radiation detecting means at a second fixed angle of view such that the means for generating generates radiation data based on radiation detected at the second fixed angle of view along the straight line path; and image reconstruction means for reconstructing an image representation of a region of interest of the subject based on the radiation data from the first and second fixed angles of view.

12. The diagnostic imaging system as set forth in claim 11 further including a means for determining coincidence radiation events detected by the radiation detecting means.

13. The diagnostic imaging system as set forth in claim 11 wherein the radiation detecting means includes means for collimating radiation.

14. The diagnostic imaging system as set forth in claim 11 wherein the radiation detecting means includes a plurality of radiation detectors angularly disposed to each other.

\* \* \* \* \*